United States Patent [19]

Horodysky et al.

[11] 3,944,539

[45] Mar. 16, 1976

[54] PREPARATION OF SULFURIZED OLEFINS

[75] Inventors: Andrew G. Horodysky, Cherry Hill, N.J.; Paul T. Allen, Beaumont, Tex.

[73] Assignee: Mobil Oil Corporation, New York, N.Y.

[22] Filed: Dec. 22, 1972

[21] Appl. No.: 317,868

[52] U.S. Cl. ............................... 260/139; 252/46.3
[51] Int. Cl.[2] ......................................... C07G 17/00
[58] Field of Search .................................... 260/139

[56] References Cited
UNITED STATES PATENTS

| | | | |
|---|---|---|---|
| 2,249,312 | 7/1941 | Kimball | 260/139 |
| 2,312,750 | 3/1943 | Cohen | 260/139 |
| 2,380,072 | 7/1945 | Reid | 260/139 |
| 2,767,163 | 10/1956 | Peters | 260/139 |
| 2,786,829 | 3/1957 | Stevens et al. | 260/139 |
| 3,068,218 | 12/1962 | Beretvas et al. | 260/139 |
| 3,243,424 | 3/1966 | Lawrence et al. | 260/139 |
| 3,471,404 | 10/1969 | Myers | 260/139 |
| 3,673,090 | 6/1972 | Waldbillig et al. | 260/139 |
| 3,697,499 | 10/1972 | Myers | 260/139 |
| 3,703,504 | 11/1972 | Horodysky | 260/139 |
| 3,703,505 | 11/1972 | Horodysky | 260/139 |

*Primary Examiner*—Lewis Gotts
*Assistant Examiner*—D. R. Phillips
*Attorney, Agent, or Firm*—Charles A. Huggett; Raymond W. Barclay; Claude E. Setliff

[57] ABSTRACT

In preparing organic sulfides by reacting olefins (e.g., butylenes) with a sulfur halide to form a sulfohalogenated intermediate which is subsequently sulfurized and dehalogenated by reaction with an aqueous solution of an alkali metal sulfide compound to form a noncorrosive organic sulfide product of high sulfur content, blackening of both the intermediate and the final product is prevented by employing an inert gas as a purge during formation of the olefin-sulfur halide adduct.

8 Claims, No Drawings

PREPARATION OF SULFURIZED OLEFINS

BACKGROUND OF THE INVENTION

1. Field of the Invention

This invention relates to the preparation of organic sulfide compounds of improved color from olefinic materials.

2. Prior Art

Various proposals have been made for producing organic sulfides by treating olefins with sulfur chlorides and then reacting the resulting intermediate with compounds containing sulfur. For example, organic polysulfides may be prepared by the sulfochlorination of olefins containing 6 or more carbon atoms and further treatment with inorganic higher polysulfides according to Eby U.S. Pat. No. 2,708,199. In addition, Myers U.S. Pat. No. 3,471,404 discloses that sulfurization reactions of this nature may be carried out by reacting a sulfochlorinated isobutylene intermediate product with a mixture of an alkali metal sulfide and free sulfur in a molar ratio of at least 2:1 followed by a further prolonged treatment with aqueous sodium hydroxide, apparently for reducing high chlorine contents, in producing extreme pressure additives. Beretvas et al U.S. Pat. No. 3,068,218 indicates that sulfochlorinated products of improved color may be obtained by sulfochlorinating polymers of propylene, etc. containing 8 or more carbon atoms in an aqueous reaction mixture and then sulfurizing the intermediate with a solution of sodium sulfide in water and isopropanol in producing products with sulfur contents of the order of 10 to 34 % by weight. In Kimball U.S. Pat. No. 2,249,312, the sulfochlorinated adduct of amylene or higher olefins is treated with sodium sulfide and/or other alkaline compounds to produce stable products of relatively low sulfur content and generally high chlorine contents.

In general, prior art organic sulfide compounds have one or more such undesirable characteristics as high cost, low sulfur content and corrosive attack on metals and alloys used in machinery. Products having a chlorine content above 2% and also those produced from sodium polysulfide reactants are usually rather corrosive. These disadvantages can be overcome and organic sulfide compounds having improved properties, especially as to high sulfur content and low corrosion characteristics, obtained by the economical process described in application Ser. No. 2,349 filed on Jan. 12, 1970 by A. G. Horodysky in which the aqueous alkali metal monosulfide reactant employed in the final reaction is derived from a spent effluent stream resulting from hydrocarbon purification operations and consequently of low commercial value. However, it has been found that a very dark or black product is occasionally obtained in that process with some olefinic hydrocarbon reactants, and the same undesirable product coloration is believed to occur quite frequently in the aforesaid prior art methods. While there is no evidence that the black color in any way reduces the effectiveness of the material as an additive for extreme pressure lubricants, such discoloration does seriously affect its marketability. Customers have a strong aversion to accepting a black product, particularly when the normal color of such material is yellow or orange or light red. The instant invention is based upon the discovery of a technique for inhibiting such discoloration of the product.

SUMMARY OF THE INVENTION

The present invention is concerned with a process of preparing organic sulfides by sulfohalogenating an olefin with a sulfur halide to form a sulfohalogenated organic intermediate and thereafter sulfurizing and dehalogenating said intermediate by subsequent reaction with an alkali metal sulfide, and the invention is characterized by the improvement which comprises employing an inert gas as a purge prior to any substantial darkening of the olefin-sulfur halide adduct and prior to said subsequent reaction.

DESCRIPTION OF SPECIFIC EMBODIMENTS

The inert gas treatment of this invention serves to inhibit the excessive darkening or blackening of reaction mixtures for the sulfohalogenation of organic compounds in general and also to stabilize the color of the resulting adducts during prolonged storage; accordingly, it may be used in conjunction with any processes that involve the sulfohalogenation of olefinic materials. Thus, it can be utilized in any of the aforementioned and other prior art processes in which olefins are sulfohalogenated and subsequently subjected to a sulfurization-dehalogenation reaction in the production of organic sulfides, for discoloration or blackening frequently occur in these processes even when moderate temperatures, good catalysts and relatively pure reactants are employed. The novel treatment is particularly suitable for use in the economical process described in the aforesaid application Ser. No. 2,349 of producing organic sulfides of high sulfur content and excellent characteristics as an extreme pressure additive by providing a consistently light-colored product which is readily saleable. Consequently, the inert gas treatment is described hereinafter mainly in respect to that process.

A wide variety of olefinic substances may be charged to the initial or sulfochlorination reaction including olefins with terminal or internal double bonds and containing from about 2 to 8 or more carbon atoms per molecule in either straight, branched chain or cyclic compounds, and these may be exemplified by ethylene, propylene, 1-butene, cis and trans-2-butene, isobutylene, diisobutylene, triisobutylene, the pentenes, cyclopentene, the hexenes, cyclohexene, the octenes, 1-decene, etc. In general, $C_{3-6}$ olefins or mixtures thereof are preferred for preparing sulfurized products for use as extreme pressure additives as the combined sulfur content of the product decreases with increasing carbon content, and the miscibility of the product with oil is lower in the case of propylene and ethylene derivatives.

In some embodiments of the invention, isobutylene is particularly preferred as the predominant olefinic reactant but it may be employed, desirably in major proportion, in mixtures containing one or more other olefins; moreover, the charge may contain substantial proportions of saturated aliphatic hydrocarbons, as exemplified by methane, ethane, propane, butanes, pentanes, etc. Such alkanes are preferably present in minor proportion in most instances to avoid unnecessary dilution of the reaction, since they neither react nor remain in the products but are expelled in the off-gases or by subsequent distillation. However, mixed charges can substantially improve the economics of the present process since such streams are of lower value than a stream of relatively pure isobutylene.

Volatile olefins are often readily available in liquid form, and it is usually desirable to charge olefinic liquids which are vaporized by the heat of reaction, as such evaporation provides a substantial cooling effect that permits the flow of water for cooling the reactor to be reduced considerably for greater economy. Also there are indications that the use of a volatile liquid olefin reactant has the unexpected and desirable effect of lowering the viscosity of the final product.

The other reactant in the first stage is preferably sulfur monochloride ($S_2Cl_2$); but other similar compounds such as sulfur dichloride and $S_3Cl_2$ as well as the corresponding but more expensive sulfur bromides may be employed in an amount which will provide a quantity of sulfur corresponding to desirable reactant ratios for sulfur monochloride. The molar ratio of olefin to sulfur monohalide may range from about 1:1 up to 1.65:1 or more. In the case of butylenes and sulfur monochloride, the optimum ratio appears to be between about 1.55:1 and 1.60:1.

Although anhydrous reaction conditions are generally regarded as providing better results, a small amount of water ranging up to about 1% of the weight of the sulfur halide may be present in the initial reaction; however it is usually preferred to keep the water content below about 0.5% on that basis.

The sulfohalogenation reaction is exothermic, evolving 500–650 btu./lb. in the case of isobutylene, and cooling is necessary to prevent the temperature from exceeding about 160°F. with resultant darkening of the product and some decrease in the yield. The preferred range of reaction temperatures is from about 120° to 135°F. and a temperature of about 125°F. appears to be the optimum. Typical reaction times for the initial stage of the process range from about 1 to 15 hours.

The reaction pressure is not critical here and may be illustrated by pressures ranging from about 0 to 100 pounds per square inch gage pressure (psig.) depending upon the reaction temperature and the volatility of the olefinic material.

The initial reaction may be catalyzed with a lower aliphatic alcohol containing from 1 to 4 carbon atoms, as exemplified by methanol, ethanol, propanol and isopropanol. Of these, methanol and ethanol are usually preferred, especially the former. An amount of the alcohol ranging from about 0.2 to 10% of the weight of the sulfur chloride may be utilized, but quantities of the order of 0.5 to 3% are usually preferred. While the catalytic alcohol may be introduced into the reactor in the liquid state, it is often more desirable to introduce it as a vapor.

Hydrogen chloride is evolved in the reaction and this gas is vented from the reactor. It may be recovered as hydrochloric acid in a water absorption system.

The inert gas must be used in the sulfohalogenation reaction mixture or the product of that reaction in preventing or at least in minimizing discoloration therein. In any event, the inert gas should be added before an undesirable dark color appears, because the treatment is not capable of restoring the original light color after the dark coloration has developed. In other words, no decolorizing of either a highly colored reaction mixture or product upon introducing the inert gas has yet been observed. A wide variety of inert gases may be employed for the purpose, provided only that the gas is compatible with the selected sulfur halide. Suitable compatibility is evidenced by the absence of substantial darkening or blackening in a mixture consisting entirely of the gas and the sulfur halide when heated to the sulfohalogenation temperatures disclosed herein for a substantial period, such as an hour or more. It is probably safe to say that any gas that will not react will suffice.

Neither the darkening of the reaction mixture or product nor the manner in which the addition of the gas prevents such discoloration is fully understood. Employing excessively high temperaures in the reaction will blacken the sulfohalogenation mixture, but darkening from this cause can readily be avoided by using the moderate reaction temperatures mentioned earlier. However, there are obviously other causes, as blackening occurs occasionally even when the reaction temperature is relatively low. There is some reason to suspect that 1-butene and trans-2-butene tend to promote discoloration or blackening in these reactions. On the other hand, olefin charges of high isobutylene content seem less prone toward darkening. In some cases, blackening has been observed in the reaction mixture and in other cases it has developed during the storage of a bright clear adduct, sometimes within about 2 hours and sometimes overnight. Blackening of the subsequent sulfurization-dehalogenation reaction and of the final product does not occur unless the adduct reactant is already badly discolored. Also, light-colored final products display no tendency to darken during prolonged storage.

While the present discovery should not be regarded as restricted to any particular theory, it may be possible that the undesirable blackening of the adduct is produced by an acid-catalyzed reaction wherein the hydrogen chloride evolved in sulfochlorination serves as the catalyst, and also that treating the mixture with an inert gas according to the present invention serves to remove the hydrogen chloride dissolved in the liquid reaction mixture and thereby inhibit such catalytic action. Even though a large amount of hydrogen chloride is produced in the reaction, very little of it remains in solution by reason of its low solubility in the reaction liquor as well as the fact that olefins bubbling through the reaction mixture tend to sweep out the hydrogen chloride as a gas.

In an integrated refinery, aqueous caustic alkali solutions are widely employed in the liquid phase purification of a variety of hydrocarbon streams, and the spent aqueous liquors resulting from such operations may be classified as "inorganic caustics" and "organic caustics". The spent inorganic caustic solutions usually have a relatively low content of organic compounds and are generally obtained from treating liquid propane, butane, butylene, solvent naphthas and alkylation effluents for the removal of mercaptans, sulfuric acid and especially hydrogen sulfide. As for the spent organic caustic liquors issuing from the treatment of catalytic gasolines and heavier distillates, these aqueous solutions contain somewhat smaller amounts of the sulfide impurities but large proportions (e.g., over 25% by weight) of organic material, chiefly in the form of aromatic derivatives, such as phenolic and thiophenolic compounds. Although potassium hydroxide is operative for such purification, sodium hydroxide solutions are invariably used for economy. After mixing all of the spent caustic solutions in a typical refinery, the approximate composition of the mixture designated herein as Promor SAS-2, may be exemplified as:

| | Weight % |
|---|---|
| sodium hydroxide | 6.1–6.3 |
| sodium hydrosulfide | 4.9–5.4 |
| sodium cresylates* | 14.6–20.4 |
| sodium sulfate | 0.5–0.7 |
| sodium chloride | 0.04–0.06 |
| oil | 0.3–0.4 |
| ferrous sulfide | (5–10 ppm.) |
| water | balance |

*sodium salts of cresols, thiocresols, phenol, thiophenol and the xylenols.

The largest component of the solute in these mixed spent solutions is the sodium cresylate mixture which is readily marketable after being recovered in the form of crude cresylic acids. The recovery can be accomplished economically by treating the caustic solution with the by-product or waste hydrogen sulfide from a catalytic hydrodesulfurization unit. This treatment springs the cresylate salts as an organic phase by conversion into cresylic acids, and it also converts the sodium sulfide and sodium hydrodide in the aqueous phase into sodium hydrosulfide. Upon standing, the mixture forms two layers with the upper layer varying in color from amber to black and containing the cresylic acids and other organic compounds while the bottom layer of aqueous sodium hydrosulfide solution separates cleanly as a milky white or colorless liquid which is drawn off for use in the present process. Thus, the hydrogen sulfide treatment not only separates valuable cresylic and thiocresylic compounds and disposes of unwanted hydrogen sulfide but also has the desirable effect of substantially increasing the sulfur content of the aqueous phase for use in the present process.

The hydrogen sulfide treatment is usually carried essentially to completion as indicated by a pH value of about 8.0–8.5, whereupon only a small content of organic compounds remain in the aqueous phase. However, in some instances, the $H_2S$ addition may be terminated earlier, for example, when the alkali metal hydrosulfide content reaches at least about 75% by weight of the dissolved alkali metal compounds. In the latter procedure, slightly more of the cresylic compounds are retained in the aqueous solution and also in the organic sulfide final product of this invention, and such retention may be desirable in view of the known antioxidant properties of alkylated phenolic compounds.

The aqueous phase derived from such treatment has a typical analysis by weight of:

| | |
|---|---|
| sodium hydrosulfide | 16–24 |
| sodium monosulfide | 0–4 |
| sodium carbonate | 1–3 |
| raw cresylic acids | 0.1–1.0 |
| sodium sulfate | 0.7 |
| sodium chloride | 0.05 |
| water | balance |

In preparing the sulfurizing reactant of the present process, this solution is then treated with a stoichiometric amount of sodium hydroxide (i.e., one mole of NaOH per mole of NaHS) or up to about a 5% excess thereof which usually raises the pH to 10–10.5 in converting the sodium hydrosulfide to sodium monosulfide.

While it is usually preferable to employ an alkali metal surfide reactant derived from a mixture of both the organic and inorganic types of spent caustic alkali solutions, substantial benefits are obtainable with a reactant prepared from spent caustic effluent of the inorganic type only. The same manner of preparation in the latter case except that there is seldom, if ever, any phase separation after the hydrogen sulfide treatment.

A lower aliphatic alcohol is generally added as a mutual solvent for the sulfurization-dechlorination reaction. Methanol, ethanol, propanol, butanol and isobutanol as well as mixtures thereof may be employed for the purpose, and isopropanol is preferred. Although a quantity of alcohol amounting to 10% of the weight of the sulfohalogenation adduct provides adequate solvent action in the reaction mixture, surprising effects are obtained with larger proportions of the alcohol in the reaction mixture in that more alcohol up to a quantity of about 50% of the weight of the adduct not only provides an unexpected increase in the reaction rate but also a striking improvement in sharply reducing the content of undesired chlorine in the final product while increasing its sulfur content. Thus it is desirable to charge at least 20% alcohol and the range of about 25 to 40% is preferred. While larger proportions of alcohol may provide some additional benefit, the cost of handling and recovering the extra alcohol also increases.

In sulfurizing and dechlorinating the sulfochlorination addition product, the aqueous alkali metal monosulfide solution is desirably present in at least a stoichiometric quantity, and preferably a slight excess, of available alkali metal in order to remove essentially all of the combined chlorine from the adduct. In practice, the adduct or intermediate product from the sulfochlorination reaction is pumped into the solution of sodium monosulfide in water and the alcohol in an amount usually ranging from 2.52 to 2.70 pounds of adduct per pound of the sodium sulfide (anhydrous basis) in providing a slight excess of available sodium.

In general, this treatment of the adduct may be carried out at temperatures between about 150° and 250°F. and the range between about 170° and 195°F. is usually preferred. The reaction pressure may be subatmospheric or elevated up to 50 or more psig. For simplicity, it is usually preferable to carry out the reaction at reflux temperature of typically 175° to 185°F. under atmospheric pressure in a vessel equipped with a reflux condenser.

The second reaction is continued with occasional sampling of the reaction mixture until the organic phase that separates upon standing is found to have a suitably low content of combined chlorine usually below 0.5% by weight and often less than 0.2%. Typically this may require from about 1 to 3 hours under preferred conditions depending upon a number of factors including the reaction temperature and the proportion of isopropanol or other alcohol present in the reaction mixture, but longer reaction times may be employed if desired.

When the chlorine has been reduced to the selected level, the reaction mixture is allowed to stand and separate into a lower aqueous sodium chloride layer and an upper liquid layer containing the desired organic sulfide product. After the brine layer has been drained off, the liquid organic product is usually transferred to a wash vessel wherein it is washed with an aqueous caustic alkali solution and one or more times with water, then allowed to stand until the organic and aqueous layers separate whereupon the wash water is withdrawn and discarded. The washing and separation of liquid phases may be expedited by the introduction of a substantial quantity of an organic solvent, such as hexane, benzene or petroleum ether. The caustic alkali wash treatment is not always necessary in the instant process for obtaining a product having a good copper corrosion strip rating and low chlorine content. The washed product is usually dried by heating at moderately elevated temperatures under subatmospheric pressure, and its clarity may often be improved by filtering the dried product through a bed of bauxite, clay or diatomaceous earth particles.

In addition to the advantages described earlier, other benefits are obtained by employing an alkali metal monosulfide reactant derived from spent aqueous caustic treating solutions of petroleum refinery origin, inasmuch as the organic sulfide product generally displays a higher combined sulfur content and is also less corrosive than the products obtainable by employing an aqueous solution of a commercial grade of either sodium monosulfide or sodium hydrosulfide in the sulfurizing dechlorinating reaction. The cause of this unusual effect as well as certain other aforementioned advantages of the process is not understood at the present time. Moreover, while the chemical composition of the final organic sulfide products of the instant process have not been fully ascertained, there is evidence that they contain a high proportion of -S-S- linkages, and such products do not corrode copper in contrast with products containing higher polysulfide linkages.

For a better understanding of the nature, objects and advantages of this invention, reference should be had to the following examples wherein letters are employed to designate comparative examples and numerals are used for examples which illustrate the present invention but are not intended as limitations thereon. Unless otherwise stated, all proportions are set forth in terms of weight and all temperatures as degrees Fahrenheit.

EXAMPLES

The table of examples hereinafter sets forth the reaction conditions and results obtained in a series of runs wherein two olefinic mixtures were sulfochlorinated. In Example 5 the hydrocarbon charge comprised 89% of isobutylene and 10% by volume of trans-2-butene. In the remaining examples, the hydrocarbon charge mixture had the following composition by volume:

| | |
|---|---|
| propane | 0.90 |
| n-butane | 4.70 |
| isobutane | 3.20 |
| propylene | 0.10 |
| 1-butene | 28.10 |
| isobutylene | 49.90 |
| trans-2-butene | 10.50 |
| cis-2-butene | 2.40 |
| butadiene | 0.20 |
| methyl acetylene | (100 ppm) |
| | 100.00 |

The mixed butenes may contain from about 20 to about 65% isobutylene and from about 5 to about 35% of butene-1, all by volume, with corresponding amounts of the other components.

First the full charge of sulfur monochloride was poured into a closed, glass lined vessel equipped with an agitator, a gas sparger, an external jacket for controlling the temperature by circulating heating or cooling fluids, and a vent line at the top for discharging gaseous material to a caustic soda scrubber. The vessel was equipped with a separate subsurface to introduce the inert gas. The olefinic charge was then introduced in vapor from along with a small amount of vaporized methanol through the submerged sparger until the absorption of olefins in the reaction mixture reached a total of typically about 1.6 moles per mole of sulfur monochloride therein. The inert gas sparging was begun before addition of olefins and was continued until absorption of olefins was complete. Continual stirring was maintained during this exothermic reaction which was catalyzed by the methanol, and the vessel was cooled with water to maintain the reaction temperature at the level set forth in the table. Hydrogen chloride evolved in this step was vented along with unreacted hydrocarbons, such as butane, to the scrubber.

The sodium monosulfide solution employed as the sulfurizing-dechlorinating reactant for the subsequent reaction was prepared from a refinery hydrosulfide solution. The hydrosulfide solution was the aqueous phase separated from an overall refinery mixture of spent caustic soda solutions of the inorganic and organic types after treatment with hydrogen sulfide in the manner described hereinbefore to produce an aqueous solution of chiefly sodium hydrosulfide with some sodium monosulfide and the minor amounts of other components mentioned earlier. Caustic soda was added to the hydrosulfide solution to convert all of the hydrosulfide and provide a charge solution containing 27% of sodium monosulfide in water.

For the sulfurization-dechlorination reaction, the sodium sulfide solution and isopropanol were charged to a stirred vessel equipped with a jacket for temperature control and heated to approximtely the specified reaction temperature with constant stirring; then the adduct produced in the first reaction was added slowly through a dip tube extending below the surface of the liquid over a period of ½ hour while cooling water was circulated through the jacket to restrain the observed temperature exotherm. At the end of the reaction time listed in the table, the isopropanol and a substantial amount of water were distilled off and agitation was suspended to allow the liquid mixture to separate into organic and aqueous brine layers. The brine layer was discarded and the organic phase containing the product was subjected to three washes, first with an equal volume of 5% aqueous sodium hydroxide followed by two washes, each with an equal volume of water. After drying the liquid product under a vacuum of 10 inches of mercury at 200°F, it was filtered through a bed of bauxite particles. Example 1 in the following shows a complete reaction.

| EXAMPLE | 1 | 2 | 3 | 4 | 5 | 6 | 7 |
|---|---|---|---|---|---|---|---|
| ADDUCT REACTION | | | | | | | |
| Olefin | MB* | MB* | MB* | MB* | MB* | MB* | MB* |
| Total Olefin Fed, Cu. ft. | 15 | 15 | 15 | 15 | — | 15 | 15 |
| $S_2Cl_2$, gm. | 1000 | 1000 | 1000 | 1000 | 507 | 1000 | 1000 |
| Reaction Temp. °F. | 132 | 132 | 132 | 133 | 150 | 131 | 131 |
| Reaction Temp. Hrs. | 8 | 8 | 6 | 4 | 2 | 7.5 | 7.0 |
| Gas added during MB addition | $N_2$ | None | $N_2$** | None | None | $N_2$ | $N_2$ |
| Rate of Flow, SCF/hr. | 3.7 | — | 2.0** | — | — | 1.5 | 1.5 |

| EXAMPLE | 1 | 2 | 3 | 4 | 5 | 6 | 7 |
|---|---|---|---|---|---|---|---|
| Color of Adduct | Yel-Orange | Black | Black | Black | Black | Lt. Yellow | Yellow |
| SULFURIZATION | | | | | | | |
| Adduct, gms | 430 | | | | | | |
| Na₂S Source | Promor SAS-2 | | | | | | |
| Alcohol | Isopropanol | | | | | | |
| Temp, °F. | 178 | | | | | | |
| Time, hr. | 3.5 | | | | | | |

*Mixed butylenes
**Nitrogen added prior to MB addition not during fuel addition.

While the process of the present invention has been described in detail in conjunction with the treatment of a limited number of reactants under similar conditions for the purposes of valid comparisons and of fully illustrating this invention, it will be readily apparent to those skilled in the art that numerous reactants, and reaction conditions are within the purview of this invention. Accordingly, the present invention should not be construed as limited in any particulars except as may be set forth in the appended claims or requied by the prior art.

We claim:

1. In the process of preparing organic sulfides by (1) sulfohalogenating an olefin with a sulfur halide to form a sulfohalogenated organic intermediate and thereafter (2) sulfurizing and dehalogenating said intermediate by subsequent reaction with an alkali metal sulfide, the reaction in (1) being run so as not to exceed 160°F and using an olefin to sulfur halide ratio of from about 1:1 to about 1:65:1 and the reaction in (2) being run at from about 150° to about 250°F using at least a stoichiometric amount of alkali metal sulfide, the improvement which comprises purging the reaction mixture in (1) with nitrogen prior to any substantial darkening of said intermediate.

2. A process according to claim 1 wherein the olefin is a mixture predominantly consisting of butylenes.

3. A process according to claim 2 wherein the mixture comprises about 89% of isobutylene and about 10% of trans-2-butylene, both by volume.

4. A process according to claim 2 wherein the mixture comprises about 50% of isobutylene, about 28% of 1-butene and about 10.5% of trans-2-butene, all by volume.

5. A process according to claim 1 wherein the sulfur halide is sulfur monochloride.

6. A process according to claim 1 wherein the initial reaction is catalyzed with a lower aliphatic alcohol containing from 1 to 4 carbon atoms.

7. A process according to claim 6 wherein the alcohol is methanol.

8. A process according to claim 6 wherein the alcohol is present in an amount ranging from 0.2 to 10% by weight of the sulfur halide.

* * * * *